US006773774B1

(12) United States Patent
Crook et al.

(10) Patent No.: US 6,773,774 B1
(45) Date of Patent: Aug. 10, 2004

(54) MICRO-PERFORATED POLYETHYLENE ENCASEMENT

(75) Inventors: John A. Crook, Birmingham, AL (US); George L. Ash, Branchville, AL (US)

(73) Assignee: Fulton Enterprises, Birmingham, AL (US)

( * ) Notice: Subject to any disclaimer, the term of this patent is extended or adjusted under 35 U.S.C. 154(b) by 0 days.

(21) Appl. No.: 10/213,903

(22) Filed: Aug. 7, 2002

Related U.S. Application Data

(63) Continuation-in-part of application No. 09/630,195, filed on Aug. 1, 2000, which is a continuation-in-part of application No. 09/223,603, filed on Dec. 30, 1998, now Pat. No. 6,183,825, which is a continuation-in-part of application No. 08/669,111, filed on Jun. 24, 1996, now Pat. No. 6,224,957.

(51) Int. Cl.[7] .............................. F16L 9/14; F16L 9/147
(52) U.S. Cl. ..................... 428/34.7; 428/132; 428/136; 138/141; 138/146; 138/DIG. 6
(58) Field of Search ................................ 428/34.7, 136, 428/35.2, 35.7, 36.5; 138/DIG. 6, 141, 146

(56) References Cited

U.S. PATENT DOCUMENTS

| | | | | |
|---|---|---|---|---|
| 3,769,120 A | * | 10/1973 | Chandler | 156/84 |
| 4,239,830 A | * | 12/1980 | Ball | 428/136 |
| 4,939,030 A | * | 7/1990 | Tsuji et al. | 428/315.5 |
| 4,957,791 A | * | 9/1990 | Richter | 428/35.5 |
| 5,492,705 A | * | 2/1996 | Porchia et al. | 426/106 |
| 6,183,825 B1 | * | 2/2001 | Crook | 428/34.7 |
| 6,224,957 B1 | * | 5/2001 | Crook et al. | 428/36.91 |
| 6,488,998 B1 | * | 12/2002 | Crook | 428/36.91 |
| 2001/0008676 A1 | * | 7/2001 | Pelkie et al. | 428/136 |
| 2002/0102674 A1 | * | 8/2002 | Anderson | 435/174 |

* cited by examiner

*Primary Examiner*—D. Lawrence Tarazano
(74) *Attorney, Agent, or Firm*—Smith, Gambrell & Russell

(57) ABSTRACT

An improved anti-corrosive material used to protect buried and submerged metallic structure such as conduits from corrosion. The anti-corrosive material is comprised of a layer of polyolefin having a plurality of microperforations formed therein. The anti-corrosive material is preferably comprised of a low density polyethylene having characteristically strong tensile strength and elongation properties to provide conventional protection from soil, water, air, or other potentially damaging elements. The microperforations allow the anti-corrosive material to be utilizeded with cathodic protection systems to provide for a significant reduction in the amount of electrical current required to achieve cathodic protection. The present invention can be used to control corrosion without costly and easily damaged coatings or adhesives; and can be applied to metallic structures in the field prior to installation. The anti-corrosive material of the present invention may further comprise one or more antimicrobial additives incorporated therein to provide protection against microbiologically influenced corrosion.

25 Claims, 3 Drawing Sheets

MICRO-PERFORATED POLYETHYLENE ENCASEMENT

The present application is a continuation-in-part application of pending U.S. patent application Ser. No. 09/630,195, filed Aug. 1, 2000 which is incorporated herein by reference. U.S. patent application Ser. No. 09/630,195 is a continuation-in-part application of Ser. No. 09/223,603, filed Dec. 30, 1998, now U.S. Pat. No. 6,183,825 B1, which is incorporated herein by reference. Application Ser. No. 09/223,603 is a continuation-in-part application of Ser. No. 08/669,111, filed Jun. 24, 1996, now U.S. Pat. No. 6,224,957 B1, which is also incorporated herein by reference.

BACKGROUND OF THE INVENTION

The present invention relates generally to the problem of corrosion relating to buried and submerged metallic structures. In even greater particularity the present invention relates to an improved anti-corrosive protective material for use with cathodic protection systems. More particularly, the present invention relates to a protective material having microperforations that is used to encase buried conduits or other metallic structures to enhance cathodic protection and control microbiologically influenced corrosion.

Buried and submerged conduits, as well as other buried and submerged metallic structures such as tanks are ubiquitously used for storing and carrying various materials, such as water, natural gas, oil, and sewage. A major problem with buried and submerged metallic structures, or concrete with metal reinforcements, is corrosion. The severity and rate of corrosion is dependent on the type of material comprising the structure and the environment in which the structure is buried. Buried conduits in particular are an important part of the infrastructure in the United States and the world. Significant costs are involved in design, development, manufacture, and installation of water, gas, and sewage systems to ensure the longevity of buried conduits and other metallic structures. Failure of these systems from conduit corrosion represents appreciable costs. Corrosion of buried conduits and metallic structures is a major economic, environmental, and safety problem.

The control of corrosion of metals has been a quest of producers and consumers for the entire history of ferrous materials. Corrosion is the deterioration of a material, in most cases a metal, because of a reaction to its environment. Corrosion mainly occurs through an electrochemical process. For corrosion to occur, the following basic elements are required: an anode (the corroding metal); a cathode (the non-corroding metal); an electrically-conductive electrolyte in which the anode and cathode are immersed, such as ionized water or soil; and a current path connecting the anode and the cathode. Additionally, there must be an electric potential difference between the anode and cathode. When these elements are present, a complete electrical circuit referred to as a corrosion cell is formed. Through such a corrosion cell, an electric current flows from the anode to the cathode, carrying metallic ions with it and causing the anode to corrode. Corrosion protection systems seek to control corrosion by disrupting the operation of a corrosion cell.

Traditionally, buried and submerged metallic or metal reinforced structures are protected from corrosive environments by means of environmental barrier systems and/or cathodic protection systems. The materials used in barrier systems have high electrical resistance, and disrupt the corrosion cell by electrically isolating the metallic structure from the surrounding electrolyte environment. The types of barrier systems include 1) coatings that are tightly bound to the outer surface of the metallic structures, 2) wraps that are tightly fixed to the outer surface of the metallic structures using adhesives, and 3) loose polyethylene sleeves or wraps that are not bonded to the outer surface. Cathodic protection systems reduce corrosion by disrupting the difference in the electrical potential between the anode and the cathode. The principles of cathodic protection are based on minimizing the electrical potential between the anode and the cathode, as well as producing current flow in the proper direction to protect the metallic structure. This can be achieved by applying a current to the structure to be protected, such as a pipeline, from some outside source. When enough current is applied, the structure becomes a cathode in the corrosion cell, and thus a non-corroding metal. The types of cathodic protection systems are 1) impressed current systems whereby a current is supplied from an external power source or 2) sacrificial anode systems that rely on the corrosive potential of different metals, and include an anode that corrodes sacrificially to protect the metallic structure.

Bonded coatings on the outer surface of metallic structures are utilized extensively to provide barrier-type protection against corrosion. Despite their widespread use, there are significant disadvantages in the use of bonded coatings. One disadvantage is the tremendous expense associated with manufacturing of metallic structures having bonded coating. Placing a bonded coating on metallic structures requires several difficult and costly manufacturing steps, including the surface preparation of the metallic structures required prior to applying the coating, and the application process itself. These steps require the operation and maintenance of costly equipment used in metallic surface preparation and coating application. Further increasing the manufacturing costs of coated metallic structures are the costs of the coating materials, which can be significant. In addition to the initial expenses associated with manufacturing bonded coating structures, additional expenses are incurred by substantial and costly handling techniques for the finished products that are required to minimize damage to the coatings during the transportation and installation of coated metallic structures. Similar limitations are associated with wraps that are tightly fixed to the outer surface of the metallic structures using adhesives. Similar to bonded coatings, such wraps require significant costs associated with metallic surface preparation prior to application of the wraps, costs associated with the application process, and material costs associated with the use of adhesives.

Corrosion-control systems are often relied upon to protect very large surface areas of underground or submerged metallic structures, such as the case with cross-country pipelines. Another significant limitation of bonded coatings, in addition to the high costs associated with manufacturing and use, is that such coatings cannot be applied to large metallic surfaces with 100% coverage. Therefore, unprotected areas of pipe surfaces can occur, leading to disbanded areas of coating. Practice has demonstrated that even well-coated pipeline will have some coating defects, referred to as holidays, that expose bare metal to the corrosive effects of an electrolytic environment. Even if it were possible for a coated pipeline to be free of holidays, bare metal may be exposed by other physical means causing disbonding of the coating, such as pipe movements with temperature variations, soil stresses, and damage from outside sources during handling and burial. In contrast to a bonded coating system, loose polyethylene wrap, referred to as loose wraps, provide an inexpensive passive environmental barrier for corrosion control. Loose polyethylene wrap does not require metallic surface preparation, or the application and consumption of adhesive and coating materials.

To compensate for the coating defects associated with bonded coatings, it is common practice to use cathodic protection systems in conjunction with the use of bonded coating. The use of a barrier system such as bonded coatings with cathodic protection systems has the advantage of greatly reducing the operating costs of the cathodic protection system, because such a cathodic protection system need only protect the areas of bare metal exposed to the electrolytic environment at the holidays or other defects, rather than the whole surface of an uncoated metallic structure. Thus, the ongoing electrical energy consumption required to maintain cathodic protection for a coated structure can be significantly less than required to protect a bare, or uncoated structure. Cathodic protection systems can cause coatings and adhesives used with wraps to disbond from the metallic structures, causing the rate of electrical consumption utilized with a cathodic protection system to increase over time. It can be appreciated that the conventional use of bonded coatings and wraps in conjunction with cathodic protections systems comes with high costs, initially at the manufacturing-stage but continuing through increasing costs associated with the operation of the cathodic protection system.

Similar to the use of bonded coatings in conjunction with cathodic protection systems, it is advantageous to use loose wrap in conjunction with cathodic protection systems to reduce operating expenses and to provide enhanced corrosion protection. Traditionally, however, cathodic protection systems have not be used with loose wraps, because it is believed that loose wraps prevent the cathodic protection current from reaching the surface of the protected metallic structure. This belief has prevented the application of cathodic protection systems and technology with economically desirable loose wraps.

Another limitation in the prior art is the use of traditional bonded coatings or wraps with cathodic protection do not effectively address problems associated with microbiologically influenced corrosion ("MIC"). Even after utilizing all the currently available mechanisms for the prevention of corrosion there are instances where unexplained corrosion occurs in buried metal pipes and conduits. In the 1930's, the mechanisms of Microbiologically Influenced Corrosion ("MIC") were proposed by Von Wolzen Kuhr to explain corrosion initiated or accelerated by microorganisms. Since that time, studies have shown the Von Wolzen Kuhr theory to be partially valid, and it has been further established that a consortium of microorganisms contribute to many metal corrosion failures. These microorganisms, alone or more typically in combination, include as follows:

Sulphate-reducing bacteria including Desulfovibrio, Desulfobacter, and Desulformaculum. Sulphate-reducing bacteria are anaerobic and are the primary cause of Microbiologically Influenced Corrosion. Sulphate-reducing bacteria are associated with the reduction of sulphate under anaerobic conditions and an associated production of hydrogen sulfide, which creates an alkaline environment that can accelerate corrosion.

Iron-oxidizing bacteria including Gallionella, Sphaerotilus, Leptothrix, Clonothrix, and Crenotlxri. Iron-oxiding bacteria are associated with the oxidization of various forms of iron and, in some cases, an associated production of ferric chloride and an acidic environment that can accelerate corrosion.

Sulfur-oxidizing bacteria including Thiobacillus, Thiodendron, Beggiatoa, and Sulfolobus. Sulfur-oxiding bacteria are aerobic bacteria that form sulphuric acid, which is corrosive to many metals, from the oxidation of sulphur or sulphur-bearing compounds.

Slime-forming bacteria including Pseudomonas, Escherichia, Flavobacterium, Aerobacter and Bacillus.

Susan Watkins Borenstein, Microbiologically Influence Corrosion Handbook ch. 2 (1994).

Hereto, no one has effectively addressed the control of microbiologically influenced corrosion occurring in buried metal pipes and conduits, in conjunction with cathodic protection systems. For example, ductile iron pipe (DIP) typically exhibits a low risk to severe corrosion compared to other metals; however, a rapid increase in the corrosion rate can be initiated by oxygenated water, tidal action, or specific soil types such as soils containing sulfides. Because of the high costs associated with removal and replacement of corroded conduits, the industry has expended substantial resources attempting to solve this problem.

As discussed above, conduits have been traditionally covered with paint coatings, wraps, or other materials to separate the conduit surfaces from the environment. However, specialized coatings are either susceptible to deterioration by bacteria, including sulfate-reducing bacteria, or are sophisticated to the point that they are no longer cost effective. It is known that cathodic protection systems may be used to counteract microbiologically influenced corrosion, however, only by utilizing high current loads that require high ongoing energy costs. High current loads also have the disadvantage of accelerating the process of disbanding of coatings and adhesives, causing ever increasing energy consumption requirements to operate the cathodic protection system. The conventional use of cathodic protection systems in conjunction with bonded coatings or wraps does not provide effective and economical protection against microbiologically influenced corrosion.

Later, barrier films of polyethylene were used to protect DIP conduits. By insulating the exposed surfaces from soil, electrical currents, and oxygenated water, corrosion is usually controlled. However, due to improper installation, tears and punctures to the barrier film occurring during the installation and backfill process, free flow of water from tidal action, or soil or water becoming entrapped between the film and the conduit surface, actual corrosion still occurs in many cases. The industry has attempted to solve these problems by using more durable barrier films to encase the conduit surfaces, such as polyethylene and also others such as polypropylene, ethylene/vinyl acetate copolymers, vinyl acetate/vinyl chloride copolymers, and polyvinyl chloride.

The superior impact strength, tear resistance, and tensile strength of HDCLPE has reduced some of the problems associated with the installation and backfill process; however, all polyethylenes do not adequately address or control the problem of microbiologically influenced corrosion. Further, polyethylenes have a high electrical resistance and are not suitable without perforations for use with cathodic protection systems. Since heretofore there has not been an adequate alternative, present industry standards typically use either an 8 mil low density polyethylene (LDPE) film or a 4 mil HDCLPE film, a mil being equal to one thousandth of an inch (0.0254 millimeter), to wrap around the conduits for only barrier protection against corrosion.

Polyethylenes, as well as other plastic films, limit the free flow of water against the conduit surfaces, thereby reducing available oxygen. Any moisture that becomes trapped between the film and the conduit surface will eventually become deaerated. A problem arises where deaerated water levels are attained in the presence of the previously identified sulfate reducing bacteria. Many anaerobic bacteria, such as Desulfovibrio desulfuricans, thrive in certain fresh water, brackish water, sea water, sulfate soils, or warm soil conditions. These bacteria act as a catalyst to initiate or augment the rate of corrosion in an environment that is normally adverse to corrosion, and as previously noted are a primary cause of microbiologically influenced corrosion. Additionally, other types of bacteria are believed to play a part in corrosion propagation and it appears that bacteria can be responsible for degradation of some polyethylene film types. A possible solution to this problem is to treat the materials used to encase the conduit with bactericides. However, most bactericides are topical and water soluble, thereby offering only initial protection that loses their effectiveness when used in buried systems exposed to wet conditions. Since conduits are buried for decades, this would not provide adequate long-term protection.

Currently available methods do not allow the use of loose polyethylene wraps with cathodic protection systems. Further, current methods for controlling conduit corrosion do not address microbiologically influenced corrosion, or their application is technically complex and very expensive, or they are not suitable for buried conduits.

From the foregoing it may be seen that hereto, no one has adequately addressed the control of the microbiologically influenced corrosion element for the long-term protection of buried conduits. A need exists for an improved anti-corrosive material for protecting conduits buried in conditions favorable to microbiologically influenced corrosion.

SUMMARY OF THE PRESENT INVENTION

It is an object of the present invention to provide an improved anti-corrosive material which is superior to those presently used to protect buried conduits.

A further object of the present invention is to provide a corrosion control system for buried and submerged metallic structures that is simple to install, resistant to installation damage, and requires no ongoing maintenance or monitoring except for any cathodic protection system that may be used therewith.

Another object of the present invention is to provide a loose polyethylene wrap that can effectively and economically control corrosion in the presence of cathodic protection systems.

A still further object of the present invention is to provide a corrosion control system that eliminates the need for bonded coatings on buried metallic structures, including pipelines and tanks.

Another object of the present invention is to provide a loose polyethylene encasement material have a plurality of microperforations.

An additional object of the present invention is to provide an improved anticorrosive material that provides long term protection of buried conduit by controlling microbiologically influenced corrosion.

Another object of the present invention is to provide a material that contains an antimicrobial additive to control bacterial-induced or enhanced corrosion.

A still further object of the present invention is to provide a corrosion control system that will provide protection against microbiologically influenced corrosion in the presence of cathodic protection systems and/or bond coated metallic structures having holidays.

Another object of the present invention is to provide a corrosion control system that provides for mitigation of corrosion resulting from installation damage.

An additional object of the present invention to provide an anti-corrosive material having an antimicrobial additive impregnated therein such that the antimicrobial additive can migrate within the material to contact the conduit surface and thereby prevent microbiologically influenced or enhanced corrosion.

These and other objects of the present invention are accomplished through the use of an improved anti-corrosive material used to protect buried conduits from corrosion. The improved anti-corrosive material is comprised of microperforated polyethylene encasement (MPPE). Such a loose polyethylene sleeve or wrap having a plurality of microperforations can be used in the presence of cathodic protection as would a bonded coating system. It can be used in lieu of expensive and easily-damaged bonded coatings on buried cathodically protected buried or submerged metallic structures, such as pipelines. Thus, the technology can be used to reduce the cathodic protection current requirements on bare (uncoated) or other metallic structures. The use of the present invention is more cost-effective than the use of bonded coatings because there are no special metal surface preparation requirements prior to use and no special handling requirements necessary to prevent damage to bonded coatings. Because no metal surface preparation is required, there is less likelihood of damage to metal surfaces during the manufacturing process. Further, the present invention does not require the use of adhesives or coatings, and can be applied either in the field or at a manufacturing facility.

Additionally, the present invention may be used with antimicrobial additives incorporated therein to effectively control bacteria associated with microbiologically influenced corrosion, without relying exclusively on cathodic protections systems for such protection. The additives can be blended with polyethylene raw materials in a manner that disperses the material throughout the product and be insoluble in aqueous conditions. Since the additive is designed as a contact agent, a requirement of manufacture is that proper dispersion and percent content be effected to generate the proper barrier against microbial growth. The anti-corrosive agents, or antimicrobial additives, are incorporated into and dispersed throughout the conduit contacting layer such that the anti-corrosive agents can migrate within the conduit contacting layer to contact the conduit surface and prevent corrosion. This product is a new cost effective anti-corrosive material used to protect buried conduits comprising ductile iron, steel, or concrete reinforced with steel by reducing or eliminating previously unexplained failures of buried conduits caused or accelerated by microbiologically influenced corrosion.

A test program was implemented to develop the proper polyethylene film manufacturing techniques that would yield proper protective characteristics in conjunction with the use of cathodic protection systems. This product is a new cost effective anti-corrosive material used to protect buried conduits comprising ductile iron, steel, or concrete reinforced with steel that may be used with cathodic protection systems.

The present invention provides an environmental barrier of loose polyethylene wrap that allows electrical current to flow through the wrap via a plurality of micro-perforations, or perforations, formed therein. The microperforations provide a mechanism to control microbiologically influenced corrosion in the presence of cathodic protection systems and/or disbonded coatings. The microperforations, having diameters from less than 1.0 rm to up to aproximately ⅛ of an inch, are spaced along the wrap with intervals sufficient to allow adequate electrical pathways for appropriate cathodic protection system current flow. The present invention is not limited to simply overcoming the deficiencies of the prior art but introduces enhanced technical advantages in corrosion protection that were not previously available for the long term protection of buried conduits while continuing to meet established industry standards.

These and other objects and advantages of the invention will become apparent from the following detailed description of the preferred embodiment of the invention.

BRIEF DESCRIPTION OF THE DRAWINGS

A micro-perforated polyethylene encasement embodying the features of the present invention is depicted in the accompanying drawings which form a portion of this disclosure and wherein.

DESCRIPTION OF THE PREFERRED EMBODIMENT

Figure 1:
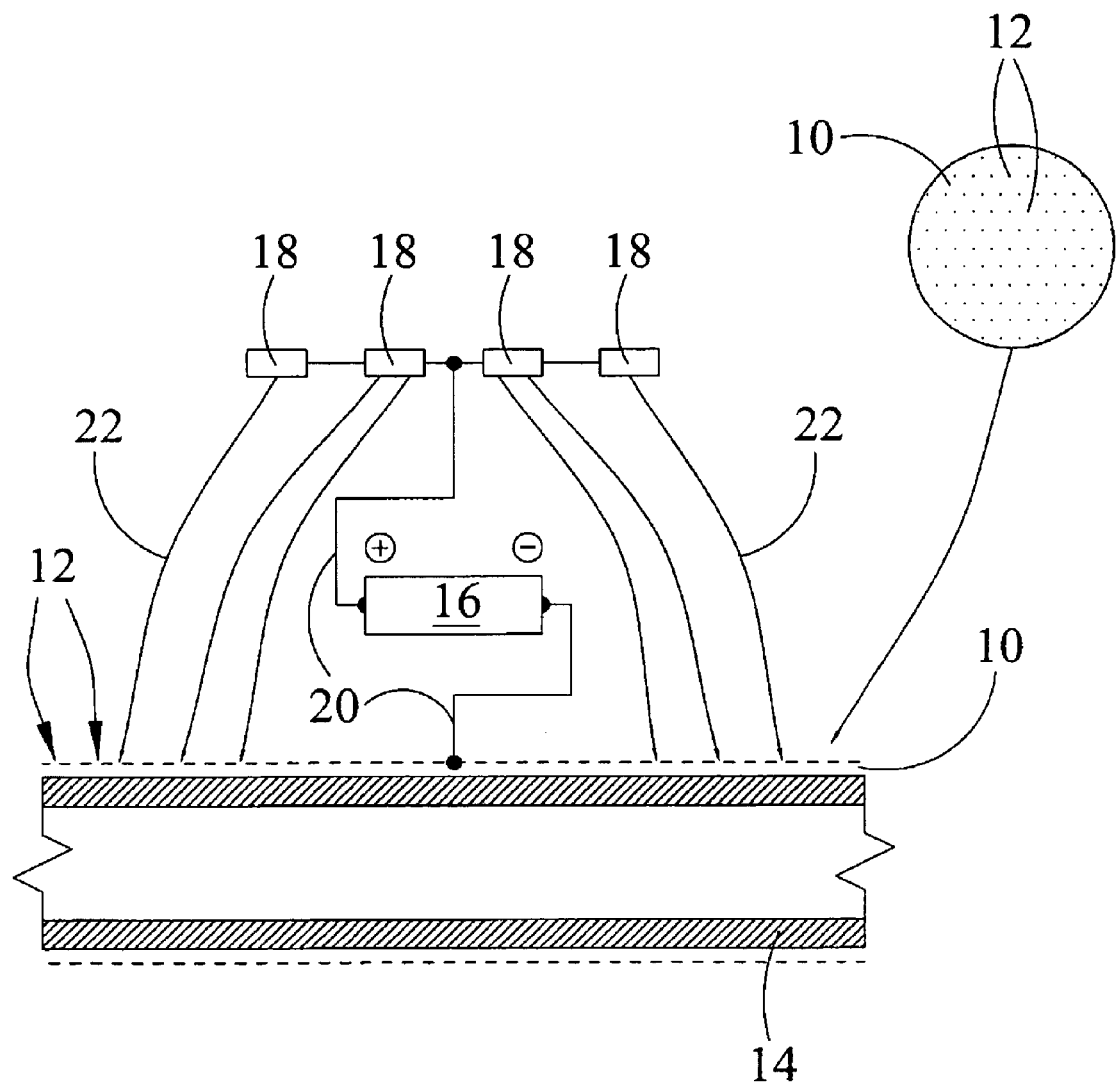
FIG. 1 is a perspective view of the preferred embodiment of a micro-perforated polyethylene encasement utilized with a cathodic protection system to protect a conduit, with an exploded view of the surface of the micro-perforated polyethylene encasement.
Figure 2:
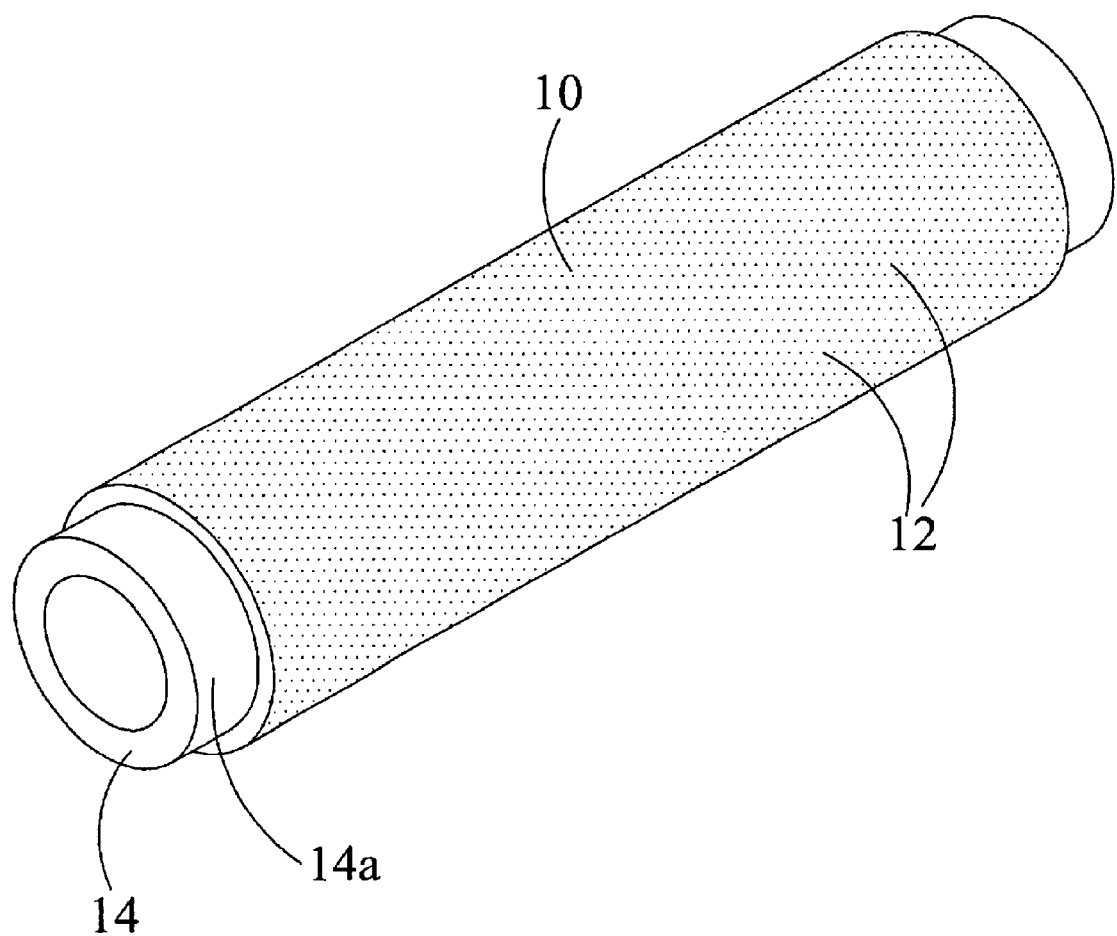
FIG. 2 is a perspective view of a micro-perforated polyethylene encasement protecting a conduit.
Figure 3:
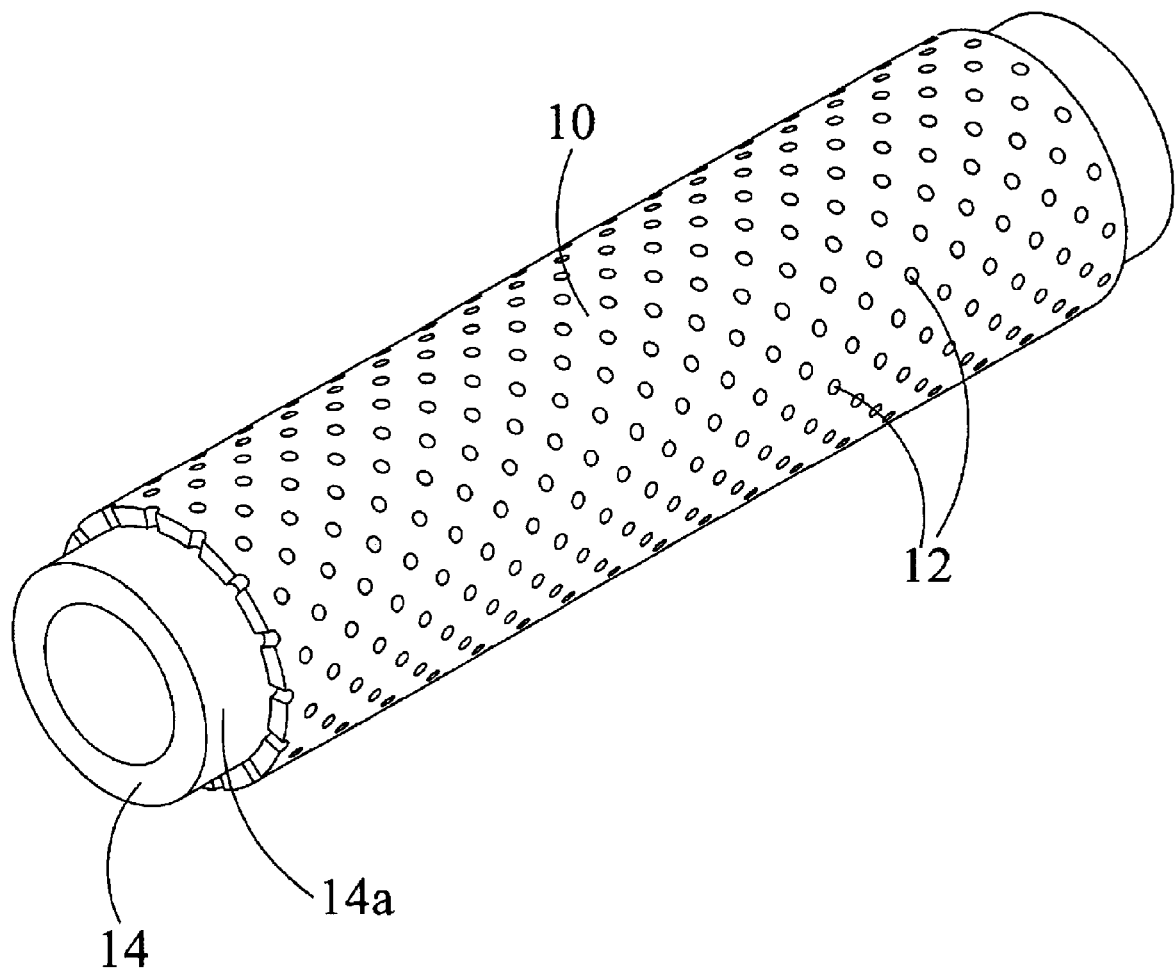
FIG. 3 is a perspective view of a second embodiment of a micro-perforated polyethylene encasement protecting a conduit, the encasement having perforations of larger diameter.

Referring to the FIGS. 1–3 for a clearer understanding of the invention, it may be seen that the invention contemplates an anti-corrosive material 10 embodying features of the invention comprising a polyolefin having a plurality of microperforations 12. As shown in FIG. 1, the preferred embodiment of the present invention is comprised of a loose wrap providing barrier protection for a metallic pipe 14, however, the present invention may be in the form of a protective film or sleeve for encasing metallic or metal-reinforced structures of various configurations to control corrosion to at least a portion of the outer surface thereof. The anti-corrosive material 10 of the preferred embodiment has a single layer with a total thickness of 8 mils, to conform to the industry standard film thickness. It is to be understood that the following description is for purposes of illustration only and that the thickness of the film or the method of making the film can be altered from that described herein without departing from the spirit of the invention. Additionally, the polyolefin of choice is polyethylene but others such as polypropylene, ethylene/vinyl acetate copolymers, vinyl acetate/vinyl chloride copolymers, or polyvinyl chloride could be substituted. Further, the present invention may have a plurality of layers, such as a material that is co-extruded, calendered, or laminated into a multilayered material.

The anti-corrosive material 10 provides conventional protection from soil, water, air, or other potentially damaging elements. It is contemplated that the anti-corrosive material 10 has a thickness of less than 1 mil to up to approximately 30 mils. In the preferred embodiment, the anti-corrosive material comprises 8 mils of low density polyethylene (LDPE), preferably linear low density polyethylene (LLDPE), having characteristically strong tensile strength and elongation properties. This deters punctures and tears to the anti-corrosive material during handling and the backfill process. LDPE has a density range between approximately 0.910 to 0.925. The anticorrosive material 10 may be manufactured utilizing any process, such as co-extrusion, calendering, or laminating to form a single or plurality of layers. The invention may comprise polyethylene, including low- (LDPE), medium-(MDPE), or high-density (HDPE) polyethylene and/or other materials such as polypropylene, ethylene/vinyl acetate copolymers, vinyl acetate/vinyl chloride copolymers, and polyvinyl chloride. MDPE has a density range between approximately 0.926 to 0.940. HDPE possesses superior tensile strength and provides a high density barrier.

The anti-corrosive material 10, also referred to as a micro-perforated polyethylene encasement (MPPE), further comprises a plurality of microperforations 12, also referred to as perforations, having a diameter from less than one nanometer to up to approximately ⅛ inch. The perforations 12 in the micro-perforated polyethylene encasement (MPPE) 10 of the present invention can be used in lieu of bonded coatings on buried cathodically protected pipelines and other buried or submerged metallic structures. As shown on FIG. 1, the anticorrosive material 10 can be used in conjunction with a cathodic protection system, because the microperforations 12 allow current flow along pathways 22 from the anode 18 of a cathodic protection system to the cathode 14 being the metallic structure protected by the cathodic protection system. FIG. 1 shows use of the present invention with a cathodic protection system of the impressed current type, whereby an electric current is generated by a power source, such as a rectifier 16, connected to the protected structure 14 and anodes 18 by electrical connection means 20. The present invention may also be utilized with other types of cathodic protection systems, including the sacrificial anode type. FIG. 1 also displays the surface of the micro-perforated polyethylene encasement 10 of the present invention.

The perforations 12 of the present invention may be randomly or uniformly spaced apart from one another, an average of less than about ⅛ inch apart to about ¾ inch apart. In the preferred embodiment, the microperforations 12 have a diameter of about 100 nanometers and are uniformly spaced apart at distances of about ⅜ inch. The preferred embodiment comprises a polyethylene encasement 10 comprising a loose polyethylene wrap for a metallic structure 14, as shown on FIG. 2. It can be seen that the preferred embodiment of the present invention provides a barrier layer for a conduit 14, and the present invention has a conduit contacting surface facing the outer surface 14a of the conduit. Also the preferred embodiment of the present invention is in the form of a loose polyethylene wrap for a conduit, it is contemplated that the present invention may be a film formed into various configurations such as sheets that can be placed under or around metallic or metal-reinforced structures to encase a portion thereof. The film may be placed below aboveground storage tanks, or around underground or submerged storage tanks to control corrosion of the outer surfaces of the structures. The present invention may also be in the form of sleeves for use in encasing structures of various configurations, such as but not limited to buried or submerged conduit comprised of metal or metal-reinforced materials including concrete with metal reinforcements. It is contemplated that the present invention may be utilized in a wide variety of configurations to enhance corrosion protection for metallic or metal-reinforced structures of various configurations.

Testing indicates that the present invention may be effectively used in lieu of expensive and easily damaged bonded coating technology for cathodic protection applications in soil contact conditions. The use of the present invention with cathodic protection systems significantly reduces the amount of electrical current required to achieve cathodic protection. Although the preferred embodiment utilizes low-density polyethylene (LDPE) having the property of low electrical conductivity, it is contemplated that the present invention may be utilized with polyethylene or other such materials modified to have the property of electrical conductivity at moderate or high levels.

The present invention can be used to reduce the cathodic protection current requirements on bare (uncoated) metallic or metallic-reinforced structures. Initial tests in 100 ohm-cm water were conducted to compare bare ductile iron pipe versus the same type pipe encased in 4 mil thick MPPE. The initial test of the MPPE of the present invention provides approximately four and one-half time less current to protect than unwrapped pipe section. Additional testing of piping encased in 4 mil thick MPPE and 8 mil thick MPPE was initiated in various types of corrosive environments which included soil and water with resistivities ranging from 500 to 2,000 ohm-cm. Controls in these tests included piping having a bonded coating of standard shopcoat, and piping encased in a standard non-perforated polyethylene. The tests indicate less current requirement or at least equivalent current requirement to achieve cathodic protection in comparison to piping having a bonded coating. The results of further testing is summarized in Table 1, which indicates that approximately two to five times less current, depending on the environment, is required to protect standard asphalt coated pipe sections wrapped in MPPE versus unwrapped sections of the same type pipe.

Table 1: Current Requirement (mA) To Achieve Cathodic Protection for Micro-Perforated Polyethylene Encasement (MPPE)

MPPE—8mil—2000 ohm-cm water—After 5 days 0.09 mA Standard Asphalt Pipe Coat—2000 ohm-cm water—After 5 days 0.93 mA MPPE—4 mil—2000 ohm-cm water—After 3 days 0.17 mA Standard Asphalt Pipe Coat—2000 ohm-cm water—After 3 days 1.13 mA MPPE—8 mil—500 ohm-cm soil—After 4 days 0.42 mA Standard Asphalt Pipe Coat—500 ohm-cm soil—After 4 days 1.73 mA MPPE—4 mil—500 ohm-cm soil—After 3 days 0.80 mA Standard Asphalt Pipe Coat—500 ohm-cm soil—After 3 days 1.87 mA The test results demonstrate the feasibility of using the present invention in place of expensive and easily damaged bonded coating technology for cathodic protection application in soil contact conditions. In addition to eliminating the costs associated with metal surface preparation and application associated with the use of coatings and adhesives used to tightly affix wraps, the present invention has the advantage of significantly reducing cathodic protection current requirements on bare (uncoated) metallic or metallic reinforced structures. The present invention allows the use of loose polyethylene encasement, or loose wraps, as an inexpensive passive environmental barrier for use in corrosion control in conjunction with cathodic protection systems. The present invention allows cathodic protection current to reach the surface of the metallic structure to be protected through the anti-corrosive material through controlled micro-perforations. The present invention provides a micro-perforated barrier system that may be used with or without additional anti-corrosive additives.

The anti-corrosive material preferably comprises an 8 mil LDPE. This layer may also be impregnated with an antimicrobial additive such as a biocide. The antimicrobial additives are incorporated into and dispersed throughout the conduit contacting layer for killing corrosion-inducing bacteria on the surface of the conduit. The antimicrobial additives must be able to withstand the temperature required to melt and process the polyolefin. In the preferred embodiment, the antimicrobial additive is 2,4,4'-trichloro-2'-hydroxy diphenyl ether (triclosan) (e.g., ULTRA FRESH®-NM-100, Thomson Research Associates, Ontario, Canada), which has been found to be effective at low concentrations against a wide range of bacteria, including those associated with microbiologically influence corrosion.

Although 2,4,4'-trichloro-2'-hydroxy diphenyl ether is the antimicrobial additive of the preferred embodiment, it is understood that another antimicrobial additive can be chosen. Other antimicrobials that either kill a broad spectrum of organisms or a specific organism associated with microbiologically influenced corrosion include bromonitropropanediol (e.g., ULTRA FRESH®-SAB, Thomson Research Associates, Ontario, Canada); organotin (e.g., ULTRA FRESH®-DM-50, Thomson Research Associates, Ontario, Canada), diiodomethylp-tolyl sulfone (e.g., ULTRA FRESH®-95, Thomson Research Associates, Ontario, Canada), halogenated aromatic nitrites, imazilil sulfate salts, 3,5,3',4' tetrachlorosalicylanilide, dichlorophene, hexachlorophene, dioxin, ethyl benzoate, methyl benzoate, and methyl phydroxy-benzoate. Some of these antimicrobial additives are presently used in kraft. See e.g., U.S. Pat. Nos. 3,469,002; 4,401,712; and 4,533,435.

The antimicrobial additive is blended into molten LDPE resin used in forming the anti-corrosive material. The LDPE and antimicrobial additive are typically mixed at about 400 degrees Fahrenheit; however, the temperature should not exceed about 425 degrees Fahrenheit because the antimicrobial additive can begin to irreversibly denature or evaporate. The molten material is then ready to be extruded to form the anti-corrosive material. The final concentration of biocide is approximately 0.01% to 10.0% by weight, with a preferred concentration of 0.5% to 2.0% although this can vary depending on the type of antimicrobial additive used and the environment to be used in. The antimicrobial additive is partially bound to the polyolefin matrix such that some antimicrobial additive is retained within the polymer matrix to prevent bacterial growth, while unbound antimicrobial additive will slowly migrate through the polymer matrix toward the conduit surface to prevent bacterial growth. The slow migration of the antimicrobial additive within the polymer matrix towards the conduit provides low levels of antimicrobial additive to the conduit surface for an extended period of time. The spirit of the present invention is providing a material comprising a conduit contacting layer having antimicrobial additives impregnated therein so that the antimicrobial additives are incorporated into and dispersed throughout the conduit contacting layer such that the anti-corrosive agents can migrate within the conduit contacting layer to contact the conduit surface and control corrosion. This material can be adapted for use with not only underground conduits but also storage tanks, building foundations, etc.

It is to be understood that the form of the invention shown is a preferred embodiment thereof and that various changes and modifications may be made therein without departing from the spirit of the invention or scope as defined in the following claims.

What is claimed is:

1. In a network of conduits for carrying fluids wherein said conduits are selected from the group consisting of metal conduits and concrete conduits with metal reinforcements, the improvement comprising: a polyolefin film for encasing one of more of said conduits within said network, wherein said film has a plurality of perforation formed in said film, said perforations having a diameter of between less than one nanometer to approximately one-eighth of an inch.

2. The improvement as described in claim 1 wherein said perforations are microperforations having a diameter of approximately 100 nanometers.

3. The improvement as described in claim 1 wherein said perforations are spaced apart at distances of between about 1/8 inch to about 3/4 inch.

4. The improvement as described in claim 3 wherein said perforations are uniformly spaced apart at distances of about 3/8 inch.

5. The improvement as described in claim 1 wherein said film has a thickness of between less than 1 mils to approximately 30 mils.

6. The improvement as described in claim 5 wherein said film has a thickness of about 8 mils.

7. The improvement described in claim 1 wherein said film is comprised of a material selected from the group consisting of low density, medium density, and high density polyethylenes.

8. The improvement as described in claim 1 wherein said film is comprised of a material selected from the group consisting of polypropylene, ethylenelvinyl acetate copolymers, vinyl acetate/vinyl chloride copolymers, and polyvinyl chloride.

9. The improvement as described in claim 1 wherein said film further comprises an antimicrobial additive incorporated into said film, said antimicrobial additive being selected from the group consisting of bromonitropropanediol, 2,4,4'-trichloro-2'-hydroxy diphenyl ether, and diiodomethyl-p-tolyl sulfone.

10. The improvement as described in claim 9 wherein said antimicrobial additive is between 0.01% to 10% by weight of said film.

11. The improvement as described in claim 1 wherein said conduit comprises ductile iron pipe.

12. The improvement as defined in claim 1 wherein said film comprises an open ended sleeve placed about at least a portion of one or more of said conduits.

13. An apparatus for carrying fluids, comprising
a conduit having an outer surface, said conduit comprising a material selected from the group consisting of metal, and concrete with metal reinforcements; and
a polyolefin film encasing said outer surface, said film having a plurality of perforations formed in said film, said perforations having a diameter of between less than one nanometer to approximately one-eighth of an inch.

14. An apparatus for carrying fluids as described in claim 13 further comprising an antimicrobial additive incorporated into said anti-corrosive film layer for killing corrosion-inducing bacteria on said outer surface of said conduit, said antimicrobial additive being selected from the group consisting of bromonitropropanediol, 2,4,4' trichloro-2'-hydroxy diphenyl ether, and diiodomethyl-p-tolyl sulfone.

15. Apparatus as defined in claim 13 wherein said film comprises an open ended sleeve placed about said conduit.

16. Apparatus as described in claim 13 wherein said perforations are spaced apart at distances of between about 1/8 inch to about 3/4 inch.

17. Apparatus as described in claim 16 wherein said perforations are uniformly spaced apart at distances of about 3/8 inch.

18. Apparatus as described in claim 13 wherein said film has a thickness of between less than 1 mil to approximately 30 mils.

19. Apparatus as described in claim 18 wherein said film has a thickness of about 8 mils.

20. Apparatus as described in claim 13 wherein said film is comprised of a material selected from the group consisting of low density, medium density, and high density polyethylenres.

21. Apparatus as described in claim 13 wherein said film is comprised of a material selected from the group consisting of polypropylene, ethylene/vinyl acetate copolymers, vinyl acetate/vinyl chloride copolymers, and polyvinyl chloride.

22. Apparatus as described in claim 13 wherein said film further comprises an antimicrobial additive incorporated into said film, said antimicrobial additive being selected from the group consisting of bromonitropropanediol, 2,4,4'-trichloro-2'-hydroxy diphenyl ether, and diiodomethyl-p-tolyl sulfone.

23. Apparatus as described in claim 22 wherein said antimicrobial additive is between 0.01% to 10% by weight of said film.

24. Apparatus as described in claim 13 wherein said conduit comprises ductile iron pipe.

25. Apparatus as described in claim 13 wherein said perforations are microperforations having a diameter of approximately 100 nanometers.

* * * * *